US00PP37394P2

(12) United States Plant Patent
Hansen

(10) Patent No.: US PP37,394 P2
(45) Date of Patent: Apr. 28, 2026

(54) ***HEUCHERA* PLANT NAMED 'Sultry Night'**

(50) Latin Name: *Heuchera hybrid*
Varietal Denomination: Sultry Night

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,868

(22) Filed: Oct. 14, 2025

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell

(57) ABSTRACT

A new and distinct hybrid of *Heuchera* plant named 'Sultry Night' has a medium-sized habit with foliage that is moderately-dissected, moderately-wavy, lightly overlapping cordate bases, light marginal undulation, glossy leaf blades of dark purplish-grey with a lighter purplish-red overlay on short petioles. The leaf blades are shallowly dissected at five main lobes with many smaller indentations. The new plant has upright, moderately-dense, branched panicles producing pinkish flower effect. The new plant is useful in the landscape or in containers.

2 Drawing Sheets

Botanical denomination: *Heuchera* hybrid.
Variety denomination: 'Sultry Night'.

STATEMENT REGARDING PRIOR DISCLOSURES UNDER 37 CFR 1.77(B)(6)

The first public introduction of *Heuchera* 'Sultry Night' was a brief description and photograph on Feb. 1, 2025, on a website maintained by Walters Gardens, Inc. Subsequently, on Jun. 3, 2025, Walters Gardens, Inc. introduced the new plant in the "Walters Gardens 2025-2026 Catalog" with a brief description and photograph. The first offer for sale of the new plant was by Walters Gardens, Inc. to North Coast Perennials on Oct. 15, 2024. Walters Gardens, Inc. obtained the new plant and information about the new plant directly from the inventor. No plants of *Heuchera* 'Sultry Night' have been sold or offered for sales in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Sultry Night'. 'Sultry Night' was hybridized by the inventor on Mar. 3, 2022, in the greenhouses of a wholesale perennial nursery in Zeeland, Michigan, USA and assigned the breeder code 22-7-6 in the trial period. The seed or female parent was the proprietary, unreleased and unnamed hybrid assigned the breeder code 21-4-4 (not patented); the male parent was 'TNHEUFR' U.S. Plant Pat. No. 29,644.

*Heuchera* 'Sultry Night' was first selected in the fall of 2023 and passed final evaluation in the fall of 2024 from among thousands of other seedlings from the same cross and other crosses. 'Sultry Night' has been asexually propagated by basal shoot cuttings at the same nursery in Zeeland, MI in 2023 and by careful shoot tip tissue culture propagation, and the resultant plants have remained stable and continued to exhibit the same characteristics as the original plant for multiple generations.

BRIEF SUMMARY OF THE INVENTION

*Heuchera* 'Sultry Night' differs from its parents as well as all other coral bells known to the applicant in the following combined traits:

1. The medium-sized, cordate, glossy leaf blades are shallowly lobed;
2. Leaves have moderately wavy margins, lightly overlapping bases, slightly folded at major veins, and light marginal undulation;
3. Leaves are dark purplish-grey with a lighter purplish-red overlay between the veins;
4. Produces medium-sized clumps and many individual leaves with short petioles producing a dense compact habit;
5. Plants have pinkish flowers on moderately dense panicles.

The most similar cultivars known to the inventor are: 'Bella Notte' U.S. Plant Pat. No. 24,291, 'Black Beauty' U.S. Plant Pat. No. 13,288, 'Black Pearl' U.S. Plant Pat. No. 29,395, 'Black Taffeta' U.S. Plant Pat. No. 26,162, 'Obsidian' U.S. Plant Pat. No. 14,836, 'Timeless Night' U.S. Plant Pat. No. 32,134, and 'Wildberry' U.S. Plant Pat. No. 31,222.

'Bella Notte' has flatter leaves with no ruffling of the foliage, the top surface is not as shiny, the coloration is more magenta without the lighter purplish-red overlay between the veins. 'Black Beauty' has a slightly larger habit with slightly larger leaves and the foliage color tends to be a lighter reddish-purple. 'Black Pearl' has larger leaves with less cupping, less wavy margins, without the lighter purplish-red overlay between the veins, and the flowers are cream-colored. 'Black Taffeta' has smaller leaves with more incised margins and the flowers are cream-colored. 'Obsidian' has smaller habit, smaller and flatter foliage with shallower incisions between the lobes, and the flowers are creamy-white. 'Timeless Night' has flatter foliage that is less dissected between the lobes, the leaves are purplish-black without the lighter purplish-red overlay between the veins, and it flowers more profusely on shorter panicles. 'Wildberry' has foliage that is smaller, flatter, less dissected, and more purplish in color and not as dark.

In comparison to the new plant, the female parent has leaves that are darker greyed-purple and more wavy margins. The male parent has leaves are flatter and less ruffled, and more purplish-red.

BRIEF DESCRIPTION OF THE DRAWINGS

The drawings of the new plant demonstrate the overall appearance of *Heuchera* 'Sultry Night' including the unique traits. The colors are as accurate as reasonably as possible with modern color reproductions. Some slight variation of color may occur because of lighting quality, intensity, wavelength, and direction or reflection.

DETAILED BOTANICAL DESCRIPTION

Figure 1:
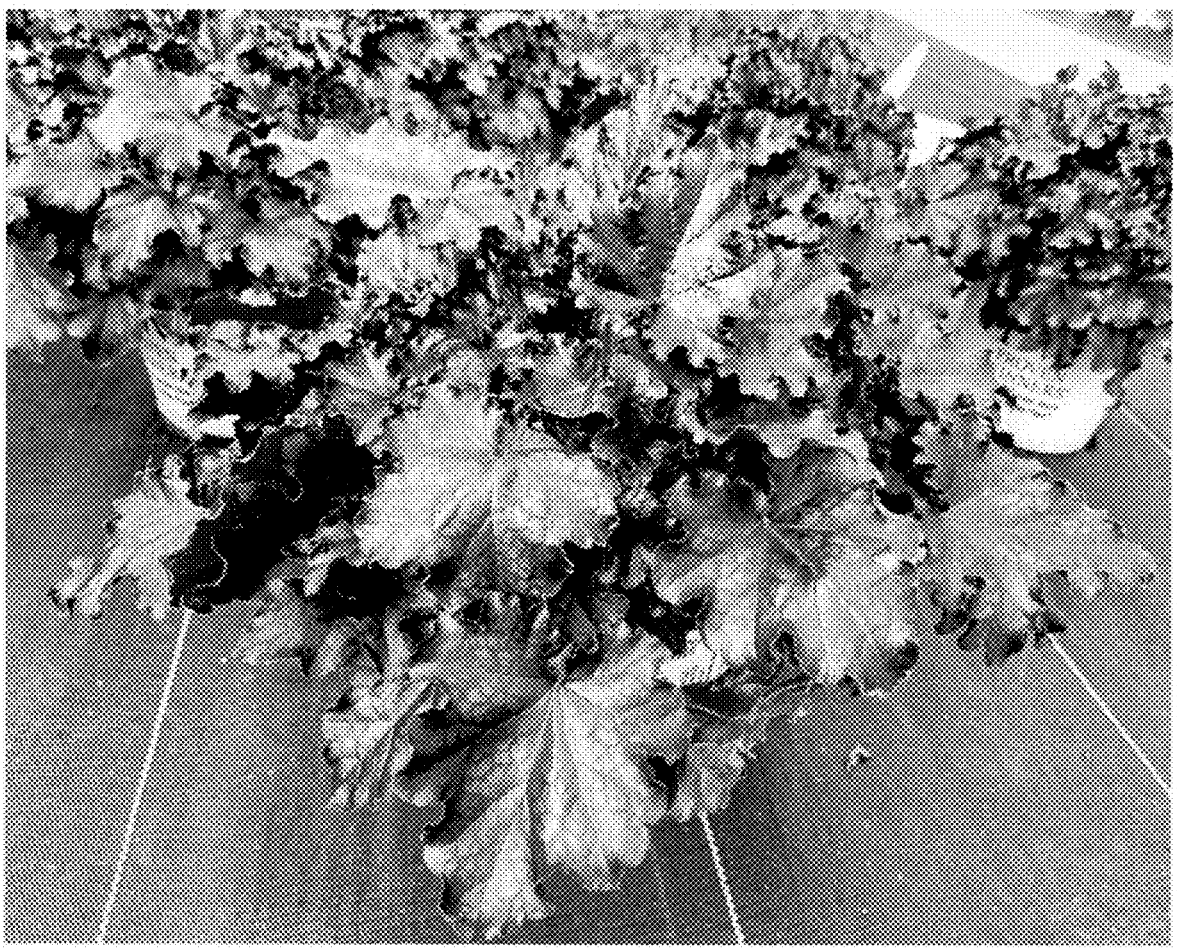
FIG. 1 shows a mature one-year-old plant in a one-gallon contain.
Figure 2:
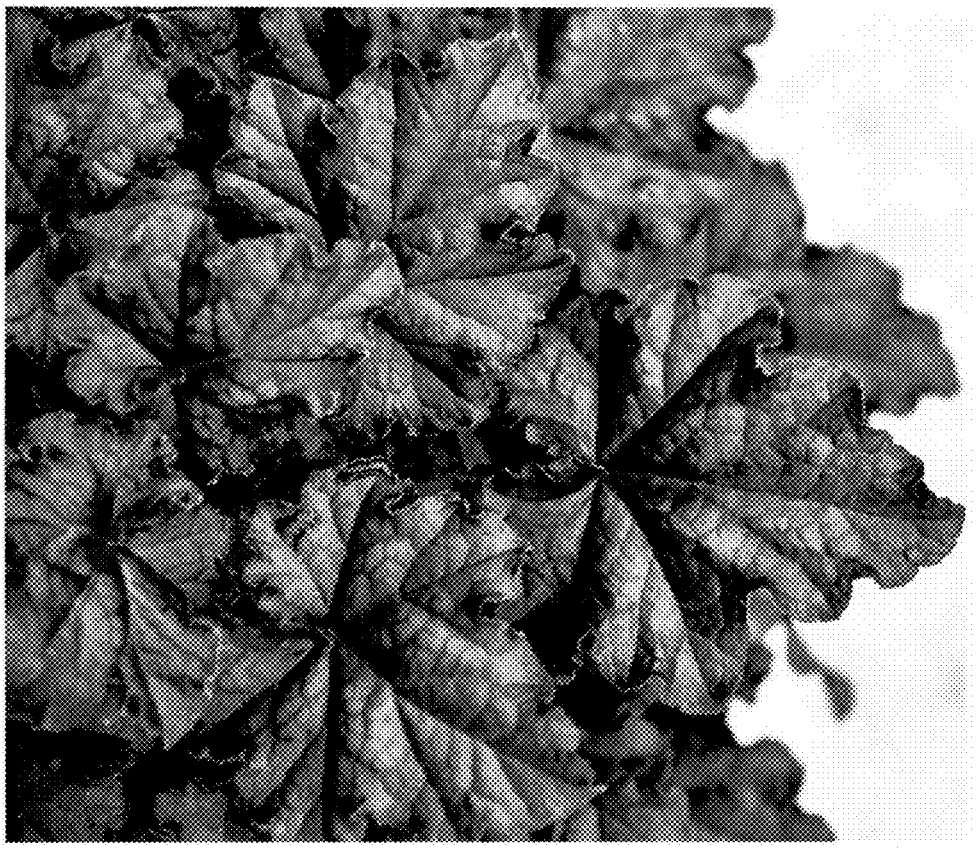
FIG. 2 shows a close-up of the foliage.
Figure 3:
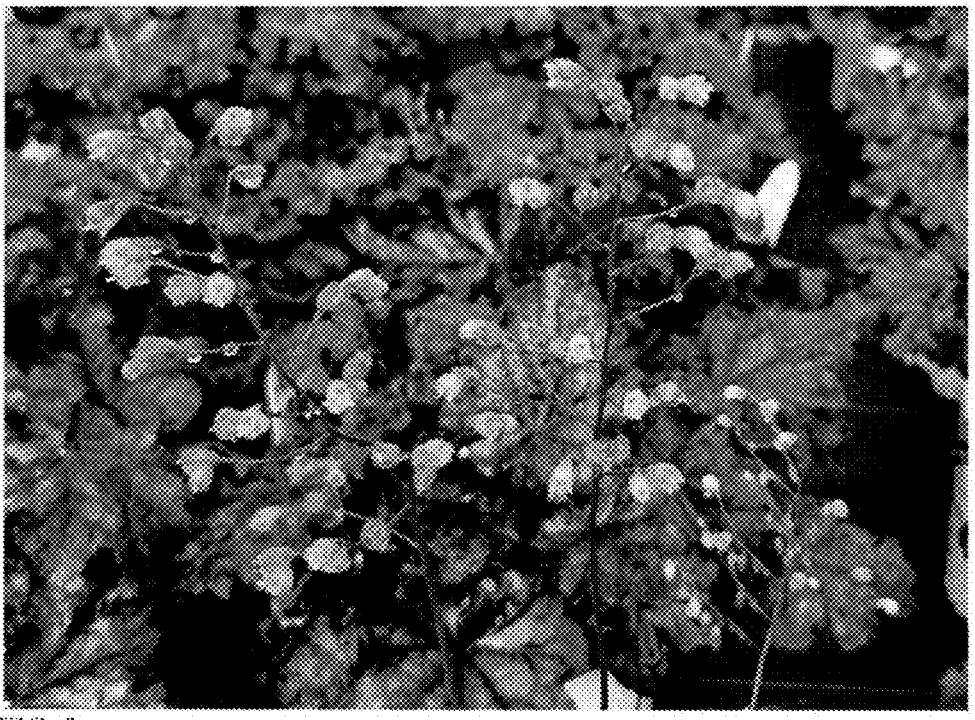
FIG. 3 shows the panicles with flowers and buds.

The following description is based on two-year-old plants growing in a lightly shaded greenhouse in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the unnamed, unreleased, proprietary hybrid known by the breeder code 21-4-4, and the male or pollen parent was 'TNHEUFR';

Plant habit: Hardy herbaceous perennial with basal rosette of foliage; mounded foliage about 21 cm tall and 39 cm in diameter with scapes to about 59 cm tall; stems to about 2 cm long and 1 cm diameter at base completely covered with petiole stipules, with about 16 leaves per stem and six main stems per plant;

Roots: Fibrous, finely branched; nearest RHS NN155B depending on soil type;

Growth rate: Vigorous, rapid; rooting from cutting in two weeks and finishing in a 3.8-liter container in about 14 weeks from a 25 mm plug;

Foliage: Cordate; shallowly penta-lobed (dissected about 15 mm deep); cordate base with basal lobes extending 30 mm beyond petiole and frequently imbricate to 5 mm; slightly folded at major veins; apex and major and minor lobe apices rounded and micro-apiculate; margin crenate and micro-ciliolate; slightly bullate in the leaf center on young leaves; adaxial and abaxial surfaces sparsely micro-puberulent, adaxial lustrous especially when young and abaxial moderately lustrous; high number of leaf indentations with four major indentations and about 30 to 40 smaller indentations; leaf margin undulation moderately;

Leaf blade size: To about 10.5 cm wide and 13 cm long, average about 11.5 cm wide and 9 cm long;

Leaf color: Seasonally variable; initial spring and expanding adaxial nearest RHS N186A with slight undertone of nearest NN137A, initial spring and expanding abaxial between but closer to RHS N186C than RHS 187B; fully expanded adaxial leaves near flowering nearest RHS N186A with small blush areas between the veins of nearest RHS N77B, fully expanded abaxial leaves near flowering abaxial leaves nearest RHS N186C; late season fall or winter have not been observed;

Veins: Palmate; sparsely hirsutulous adaxial and hirsutulous abaxial; costate abaxial and slightly concave adaxial;

Vein color: Emerging or initial spring adaxial primary veins in proximal region nearest RHS N186D and secondary and distal veins nearest RHS N186A, emerging or early spring abaxial between RHS 186A and RHS N186D; near flowering adaxial primary veins in proximal region between RHS N77B and RHS N186A and secondary veins nearest RHS 187A, near flowering season abaxial proximal main veins between RHS N77B and RHS N77C and distally and secondary veins nearest RHS 187A;

Petiole: Cylindrical; base amplexicaul; stiff; outer leaves outwardly and inner leaves slightly arcuate upwardly; hirsute with hairs to about 2 mm long; to about 10 cm long, 4 mm across at base above stipule, and 2.5 mm across below petiole, average about 8.5 cm long, 3 mm across above stipule and 2 mm across below petiole;

Petiole color: Variable with season; young emerging adaxial RHS N186D and abaxial between RHS 186A and RHS N186D; near flowering season adaxial nearest RHS N186C, and abaxial proximally between RHS 182B and RHS 148B and distally between RHS N186C and RHS N186D;

Stipule: At base of petiole; adaxial glabrous, abaxial glabrous except sparsely hirsutulous in distal center; margin ciliate; to about 18 mm long and about 10 mm wide at base and 10 mm wide at apex, with two distally-flared acute lobes about 4 mm long; margin hyaline;

Stipule color: Adaxial and abaxial lobes between RHS 60A and RHS 64A, adaxial and abaxial center between RHS 64B and RHS 64C, adaxial and abaxial hyaline margins between RHS 64D and RHS 62D;

Peduncle: Panicle; cylindrical; stiff; pubescent; upright; to about 59 cm long and 6 mm diameter at base, average about 57 cm tall and about 5 mm diameter; heavily compound branched; about four per plant; with about 600 to 900 flowers per panicle; aspect erect and upwardly;

Peduncle color: Proximally between RHS 186A and RHS N186D; distally and branches nearest RHS N186B;

Inflorescence: Compound-branched panicle with up to 30 branches to about 13 cm long and about 1 mm diameter at base, decreasing in size distally; branches upwardly and becoming more outwardly distally; flowering in upper 34 cm and 15 cm wide;

Flowering longevity: Individually to about three or four days; panicle effective for about three weeks;

Flower density: Moderately open;

Pedicel: Cylindrical; finely puberulent, to about 3 mm long and 0.3 mm diameter;

Pedicel color: Distally nearest RHS 173A and proximally nearest RHS 187A;

Buds one day prior to opening: Oblong ellipsoidal; rounded apex and attenuate base; puberulent; about 4 mm long and 2.5 mm diameter near middle;

Bud color one day prior to opening: Middle portion between RHS 63B and RHS 63C, proximal portion between RHS 185C and RHS 184D, apical portion nearest RHS 187B;

Flower: Perfect, campanulate, actinomorphic, about 7 mm long to exserted style and 4.5 mm in diameter at face; corolla to 6 mm long and 4.5 mm diameter; not persistent;

Flower aspect: Outwardly to slightly drooping;

Calyx: Five sepals; apex acute; about 6 mm long and 4 mm wide, base fused in proximal 4 mm to form hypanthium;

Sepals: Five; glabrous adaxial; puberulent to glandular abaxial; not persistent;

Calyx color: Adaxial apex nearest RHS 187B and distally nearest RHS 186C; abaxial proximally between RHS 179A and RHS 180A, distally nearest RHS 187B and middle portion nearest RHS 186C;

Petals: Five; oblanceolate overall, trifid; lobes and terminal apices acute; attenuate base; margin entire; glabrous abaxial and adaxial; adnate to adaxial sepals in proximal 1 mm; about 4 mm long and 1.2 mm wide near middle;

Petal color: Abaxial and adaxial between RHS NN155D and RHS N155B;

Androecium: Five;

*Filaments*.—Five; glabrous; adnate to adaxial calyx about 1 mm above base; thin, glabrous; about 3 mm long and about 0.2 mm diameter; adnate to adaxial sepals in proximal 1 mm; color nearest RHS NN155D.

*Anthers*.—Ellipsoidal, distinct, basifixed, longitudinal; about 1 mm long and 0.7 mm across; color nearest RHS N163B.

*Pollen*.—Abundant; color nearest RHS 12B.

Gynoecium: One, two-beaked; half-inferior; 7 mm long;

*Style*.—Bifid; exserted; split apart at apex of ovary; about 5 mm long and about 1 mm across at base; color nearest RHS NN155C.

*Stigma*.—Acute apex, about 0.2 mm diameter; color nearest RHS NN155C.

*Ovary*.—Half-inferior, about 1.5 mm long and 1.5 mm diameter; ellipsoidal to globose; apex acute, base rounded; color nearest RHS 145B.

Fruit: Two-beaked, dehiscent, ellipsoidal capsule; about 4 mm long and 2.5 mm across; color nearest RHS N199B;

Seed: Linear; about 2 mm long and 0.2 mm across; color nearest RHS N199C;

Growth: 'Sultry Night' grows best with ample moisture and drainage in either sun or shade. Cold hardy from USDA zones 4 to 9.

Disease and pest tolerance: Resistance and tolerance outside of that normal for *Heuchera* is not known.

It is claimed:

1. A new and distinct *Heuchera* plant named 'Sultry Night' as herein described and illustrated.

* * * * *